(12) United States Patent
Baig et al.

(10) Patent No.: US 12,318,180 B2
(45) Date of Patent: Jun. 3, 2025

(54) MAGNETO-OPTICAL DETECTION OF LYME DISEASE USING MAGNETIC NANOPARTICLES

(71) Applicant: CASE WESTERN RESRVE UNIVERSITY, Cleveland, OH (US)

(72) Inventors: Tanvir Baig, Shaker Heights, OH (US); Robert Deissler, Fairview Park, OH (US); Brian Grimberg, Cleveland Heights, OH (US); Robert Brown, Solon, OH (US); Michael Martens, Chagrin Falls, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 1255 days.

(21) Appl. No.: 17/081,761

(22) Filed: Oct. 27, 2020

(65) Prior Publication Data

US 2021/0068697 A1   Mar. 11, 2021

Related U.S. Application Data

(62) Division of application No. 16/134,338, filed on Sep. 18, 2018, now abandoned.

(51) Int. Cl.
*A61B 5/05* (2021.01)
*A61B 5/00* (2006.01)
(Continued)

(52) U.S. Cl.
CPC .............. *A61B 5/05* (2013.01); *A61B 5/0082* (2013.01); *G01N 33/54326* (2013.01); *G01N 33/56911* (2013.01)

(58) Field of Classification Search
CPC .. A61B 5/05; A61B 5/0082; G01N 33/54326; G01N 33/56911; G01N 33/569
See application file for complete search history.

(56) References Cited

U.S. PATENT DOCUMENTS

| | | | |
|---|---|---|---|
| 4,897,185 | A | 1/1990 | Schuyler |
| 5,238,810 | A | 8/1993 | Fujiwara |
| (Continued) | | | |

OTHER PUBLICATIONS

Chertok et al. "Iron oxide nanoparticles as a drug delivery vehicle for MRI monitored magnetic targeting of brain tumors". 2007. Biometerials 29:487-496. (Year: 2007).*
Chung, et al.; Magneto-optic measurement of Brownian relaxation of magnetic nanoparticles; Journal of Magnetism and Magnetic Materials 320; 2008; pp. 91-95.
(Continued)

*Primary Examiner* — Peter Luong
(74) *Attorney, Agent, or Firm* — Tarolli, Sundheim, Covell & Tummino LLP

(57) ABSTRACT

A system is described herein that can be used to perform magneto-optical detection of a disease component in a test sample using magnetic nanoparticles. A concentration of magnetic nanoparticles and a concentration of bindable agents can be administered to the test sample. The magnetic nanoparticles can be configured to attach to the bindable agents. A light beam can be transmitted through the test sample to a light detector. A magnetic field gradient can be established through the test sample. If the transmitted light beam under the magnetic field gradient exhibits a variable intensity change during a time period, the disease component can be determined to exist in the test sample.

11 Claims, 6 Drawing Sheets

(51) Int. Cl.
*G01N 33/543* (2006.01)
*G01N 33/569* (2006.01)

(56) References Cited

U.S. PATENT DOCUMENTS

| | | | |
|---|---|---|---|
| 5,287,681 | A | 2/1994 | Vernon et al. |
| 5,978,694 | A | 11/1999 | Rapoport |
| 7,639,359 | B2 | 12/2009 | Chung et al. |
| 8,214,006 | B2 | 7/2012 | Newman et al. |
| 8,423,104 | B2 | 4/2013 | Wiseman et al. |
| 9,575,052 | B2 | 2/2017 | Grimberg et al. |
| 9,778,245 | B2 | 10/2017 | Grimberg et al. |
| 11,698,381 | B2 * | 7/2023 | Benelmekki Erretby ............... B03C 1/288 356/436 |
| 2005/0048599 | A1 * | 3/2005 | Goldberg ............ G01N 33/561 435/287.1 |
| 2007/0161116 | A1 * | 7/2007 | Copse ................. G01N 33/569 436/172 |
| 2010/0149519 | A1 | 6/2010 | Toofan |
| 2011/0196222 | A1 | 8/2011 | Behrend et al. |
| 2012/0021456 | A1 | 1/2012 | Levine et al. |
| 2012/0257199 | A1 | 10/2012 | Liu et al. |
| 2012/0326104 | A1 | 12/2012 | Kwon et al. |
| 2015/0125873 | A1 | 5/2015 | Newman et al. |

OTHER PUBLICATIONS

Mens, et al. "Laboratory evaluation on the sensitivity and specificity of a novel and rapid detection method for malaria diagnosis based on magneto-optical technology (MOT)." Malaria journal 9.1 (Published Jul. 19, 2010).

Rosenfeld, et al., "Diagnosis of Lyme borreliosis", Clin Microbial Rev 18:484-509, https://doi.org/10.1128/CMR.18.3.484-509.2005.

Borchers, et al., "Lyme disease: a rigorous review of diagnostic criteria and treatment", J Autoimmun 57:82-115, Feb. 2015, https://doi.org/10.1016/j.jaut.2014.09.004.

Wormser, et al., "The clinical assessment, treatment, and prevention of Lyme disease, human granulocytic anaplasmosis, and babesiosis: clinical practice guidelines by the Infectious Diseases Society of America", Clin Infect Dis 43:1089-1134, 2006—https://doi.org/10.1086/508667.

Bratton, et al., "Diagnosis and treatment of Lyme disease", Mayo Clin Proc 83:556-571, 2008—https://doi.org/10.4065/83.5.566.

Binnicker, et al., "Evaluation of two commercial systems for automated processing, reading, and interpretation of Lyme borreliosis Western blots", J Clin Microbial 46:2216-2221, 2008—https://doi.org/10.1128/JCM.00200-08.

Brian T. Grimberg, Ph.D., "Manipulations of Malaria Parasites Magnets", World Health Interest Group Meeting Jan. 27, 2012, The center for Global Health and Diseases, Case Western Reserve Univ . . . .

\* cited by examiner

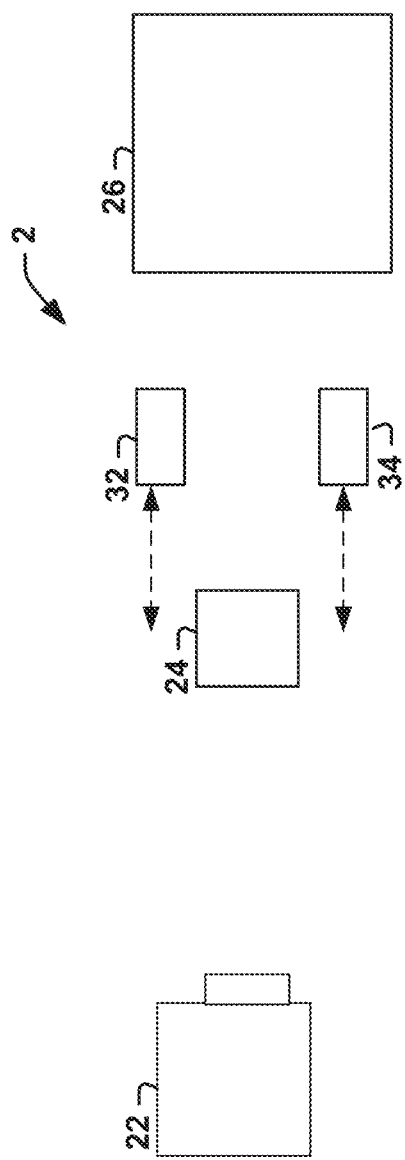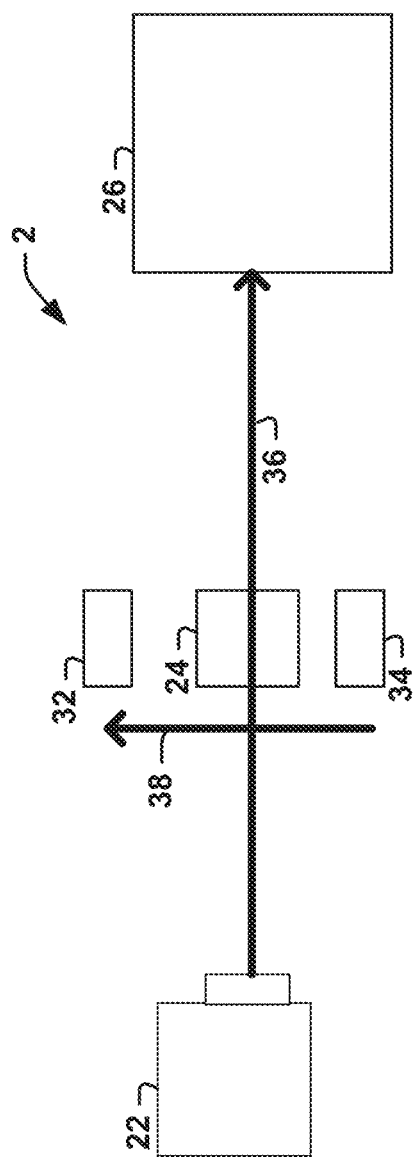

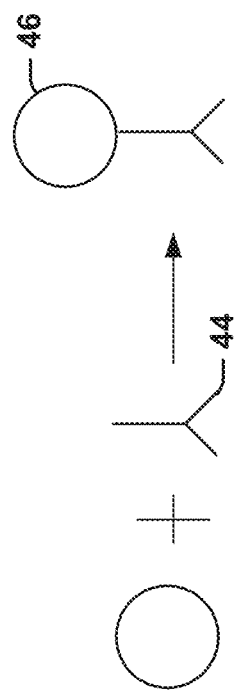
FIG. 4
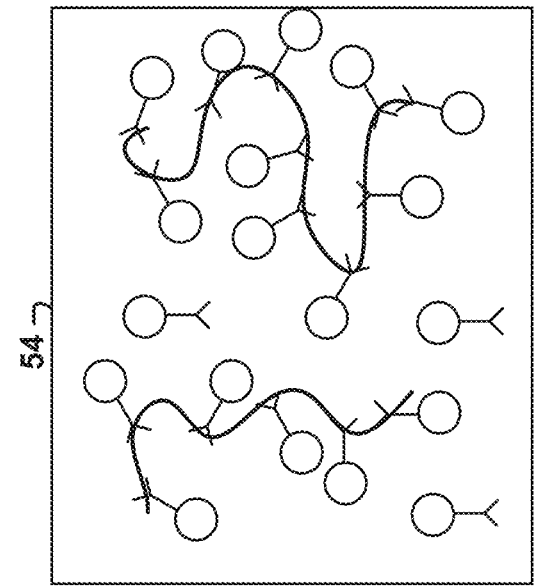
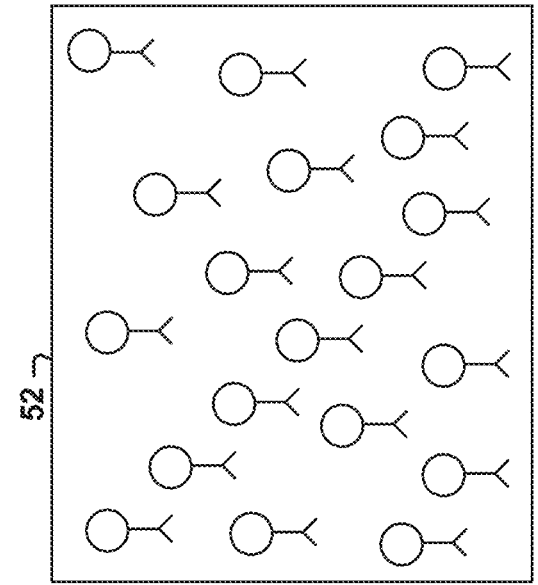
FIG. 5

MAGNETO-OPTICAL DETECTION OF LYME DISEASE USING MAGNETIC NANOPARTICLES

CROSS-REFERENCE TO RELATED APPLICATIONS

This application is a Divisional application of U.S. Ser. No. 16/134,338, filed Sep. 18, 2018, entitled "MAGNETO-OPTICAL DETECTION OF A DISEASE COMPONENT USING MAGNETIC NANOPARTICLES". The entirety of this provisional application is incorporated herein in its entirety.

GOVERNMENT FUNDING

This invention was made with government support under AI116709 awarded by the National Institutes of Health. The government has certain rights in the invention.

TECHNICAL FIELD

This disclosure relates generally to detection of a disease component and, more specifically, to magneto-optical detection of a disease component using magnetic nanoparticles.

BACKGROUND

Early and accurate diagnosis and treatment of infections or cellular abnormalities caused by bacteria, viruses, fungi, or tumors have the ability to change long term outcomes for hundreds of thousands or more patients worldwide. For example, Lyme disease, which is spread by tick bites, is an infectious disease caused by bacteria of the *Borrelia* type. Lyme disease affects an estimated 300,000 people a year in the United States alone. The symptoms of Lyme disease may include loss of movement of facial muscles, joint pains, severe headaches with neck stiffness, fatigue, and long term shooting pains and memory problems. Symptoms can often be cured if Lyme disease it treated early with antibiotics. However, current methods for diagnosing Lyme disease can be inaccurate and can take weeks to process.

The classic sign of Lyme disease is erythema chronicum migrans, a bullseye type rash that can present in 3 to 32 days after the tick bite. However, 20-30% of people infected with Lyme disease do not present this rash and are often misidentified based on other symptoms. Currently, a two-tiered serological test, using Western Immunoblot and Enzyme Immunoassay, is the standard for clinical confirmation of Lyme disease. However, this two-tiered serological test takes too much time to diagnosis Lyme disease, for example antibody titers of IgM antibody and IgG antibody take 1-2 weeks and 4-6 weeks, respectively. Lyme disease cannot be clinically detected earlier than this window. Moreover, serological test interpretation is subjective and can lead to diagnostic variation between laboratories. Polymerase Chain Reaction has also been used to study *Borrelia* bacteria, but it is not widely used to diagnose Lyme disease because of its low sensitivity. No direct detection methods are currently recommended by the CDC or approved by the FDA. A diagnostic test that can directly detect *Borrelia* bacteria, or other harmful infectious bacteria, viruses, fungi, or tumors, within the first few days of the infection would enable early stage treatment and prevent symptoms due to late stage detection of infections or cellular abnormalities.

SUMMARY

This disclosure provides systems and methods that can employ a diagnostic test that can directly detect harmful disease components, including bacteria, viruses, fungi, or tumors, at an early stage. Such early stage detection enables early-stage treatment, preventing the consequences of late stage detection.

In accordance with an aspect of this disclosure, a system is provided for detecting a disease component in a test sample using magnetic nanoparticles. The system includes a light source to transmit a light beam through the test sample to a light detector. The system also includes a magnet (e.g., a permanent magnet, a lab magnet, and/or an electromagnet) to establish a magnetic field gradient through the test sample. The test sample includes magnetic nanoparticles and a bindable agent specific to a disease component. The system also includes a measurement device that samples the light detector over a time period to determine whether the disease component exists in the test sample if a change in intensity of the transmitted light beam under the magnetic field gradient exhibits a variable intensity change pattern during the time period.

In accordance with another aspect of this disclosure, a method is provided for detecting a disease component in a test sample using magnetic nanoparticles. A concentration of magnetic nanoparticles and a concentration of bindable agents can be administered to a test sample. A light beam can be transmitted through the test sample to a light detector. A magnetic field gradient can be established through the test sample. A disease component can be determined to exist in the test sample if a change in intensity of the transmitted light beam under the magnetic field gradient exhibits a variable intensity change during a time period.

BRIEF DESCRIPTION OF THE DRAWINGS

The features, objects, and advantages of the invention will become more apparent from the detailed description set forth below when taken in conjunction with the drawings, wherein:

FIG. 2-3 are block diagram operational examples of the magneto-optical diagnostic system shown in FIG. 1 that can perform magneto-optical detection of the disease component using magnetic nanoparticles;

FIG. 4 is an illustration showing creation of a linkage between one or more magnetic nanoparticles and a bindable agent specific to a disease component;

FIG. 5 is an illustration of examples of samples with and without a disease component;

DETAILED DESCRIPTION OF THE INVENTION

This disclosure provides systems and methods that can be used to perform magneto-optical detection of a disease component (e.g., pathogenic bacteria, virus, fungi, cancer cells, or the like) using magnetic nanoparticles. The magnetic nanoparticles can be configured to attach to a bindable agent specific for a particular disease component. For example, the bindable agent can be an antibody, a ligand, an aptimer, or the like. The nanoparticles and the bindable agent can be administered to a test sample that may contain the disease component. Any disease component within the test sample can bind to the bindable agent (attached to the magnetic nanoparticles). Under a magnetic field, the disease component covered with magnetic nanoparticles can be moved (rotated and/or translated), thereby changing the amount of light that is transmitted through the test sample. Therefore, the presence of the disease component can be identified if an intensity of the light transmitted through the test sample exhibits a variable intensity change pattern during the time period. Use of the magnetic nanoparticles, which can attach to the disease component through a specific bindable agent, can make magneto-optical detection available for the direct, timely detection of the disease component in the test sample.

Figure 1:
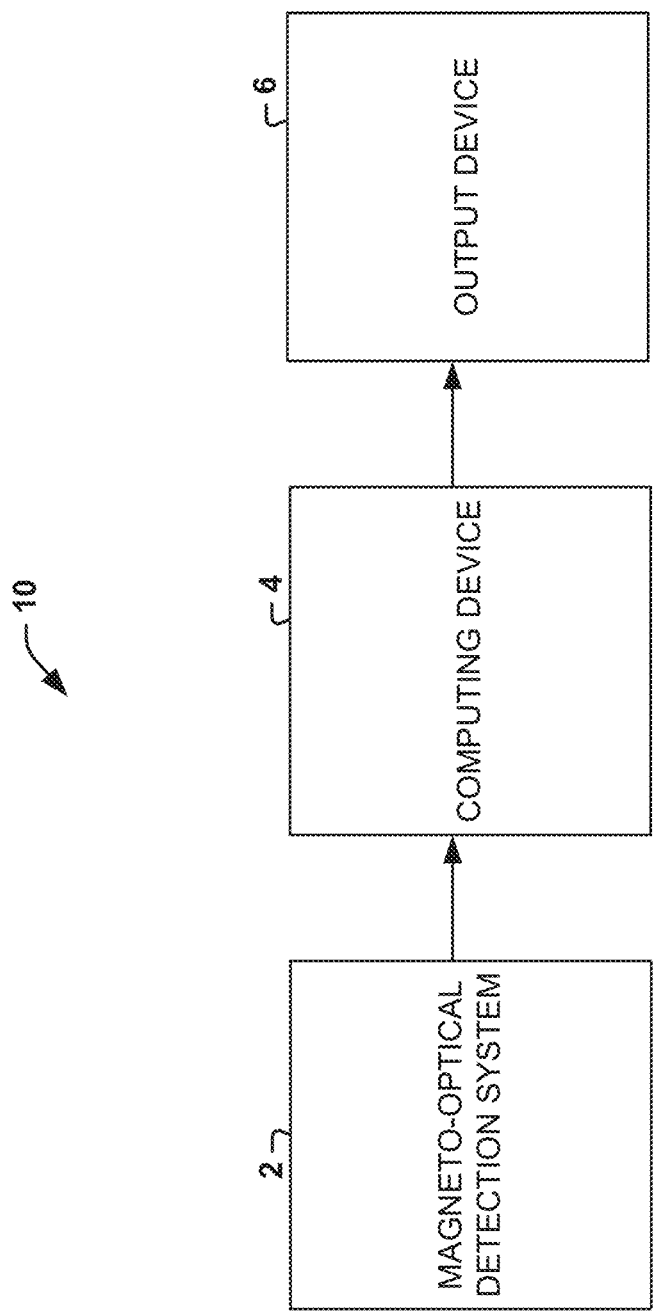
FIG. 1 is a block diagram of an example system that can determine the presence of a disease component in a test sample.

FIG. 1 shows an example of a system 10 that can determine the presence of a disease component in a test sample. The system 10 can include a magneto-optical detection system 2 to detect any instances of the disease component in the test sample. The magneto-optical detection system 2 can communicate results of the detection to a computing device 4. For example, the magneto-optical detection system 2 can detect a light signal passing through the test sample in the presence of a magnetic field gradient and communicate an output related to the detected light signal to the computing device 4. The computing device 4, which can include a non-transitory memory storing instructions and a processor to execute the instructions, can execute instructions to analyze the output. The computing device 4 can determine whether the disease component exists in the sample based on the output. However, the computing device 4 may only perform signal processing on the output and prepare the processed output for display on the output device 6. For example, the output device 6 can provide a visual display of the output. However, the output device 6 may alternatively provide an audio output, a tactile output, or an alternative visual output. The communication between the magneto-optical detection system 2, the computing device 4, and the output device 6 can be according to wired connections and/or wireless connections.

The magneto-optical detection system 2 is shown in more detail in FIGS. 2 and 3. The magneto-optical detection system 2 can include a light source 22, a measurement device 26 (which can include a light detector), and a sample holder 24 located between the light source 22 and the measurement device 26. The magneto-optical detection system 2 can also include one or more permanent magnets (two permanent magnets 32, 34 are shown in FIGS. 2 and 3, but it will be understood that the magneto-optical detection system 2 can have any number of permanent magnets and/or groups of permanent magnets greater than or equal to one).

The permanent magnets 32, 34 can also be associated with simple, inexpensive lab magnets and/or electromagnets. An electromagnet can be made from a coil of a wire that acts as a magnet when an electric current passes through it, but stops being a magnet when the current stops. The coil can be wrapped around a core of a soft ferromagnetic material, such as steel, which greatly enhances the magnetic field produced by the coil.

Generally, permanent magnets 32, 34 can produce a high magnetic field with a low mass. For example, the magnetic field can be between about 0.01 T and about 100 T. As another example, the magnetic field can be between about 0.1 T and 10 T. As a further example, the magnetic field can be between 0.1 T and 2 T. Additionally, a permanent magnet is generally stable against demagnetizing influences. For example, this stability may be due to the internal structure of the magnet. The permanent magnet can be made from a material that is magnetized and creates its own persistent magnetic field. The permanent magnet can be made of a hard ferromagnetic material, such as alcino or ferrite. However, the permanent magnet can also be made of a rare earth material, such as samarium, neodymium, or respective alloys.

The sample holder 24 can hold the test sample. The test sample can include a biofluid, which may include the disease component that can be indicative of a disease or condition. The disease component can be pathogenic bacteria, virus, fungi, cancer cells, or the like. The term "biofluid" refers to any type of fluid that includes cells originating from inside the body of a living organism. Biofluids can be excreted (such as urine or sweat), secreted (such as breast milk), obtained with a needle (such as synovial fluid, blood or cerebrospinal fluid), or develop as a result of a pathological process (such as blister fluid or cyst fluid). The biofluid may also include cells (e.g., taken by a biopsy) that can be diluted in a buffer solution. In fact, any type of biofluid may be diluted by a substance that is substantially inert (like a buffer). Additionally, the biofluid may undergo a digestive process or other chemical processes to better reveal components of the biofluid.

The biofluid being tested can be suspected of including a specific disease component. However, the disease component is normally non-magnetic and would not be detectable by the magneto-optical detection system 2. The use of magnetic nanoparticles 42, as shown in FIG. 4, can make a previously-non-magnetic disease component detectable. Generally, magnetic nanoparticles 42 can be metallic particles (e.g., containing iron or an iron-like material) sized between 1 and 100 nm in diameter. The magnetic nanoparticles 42 cannot normally attach to the disease component. However, a bindable agent 44 can be configured to interface with the specific disease component. For example, the bindable agent 44 can be an antibody, ligand, aptamer, or the like that is configured to bind to the specific disease component.

The magnetic nanoparticles 42 can include a surrounding interfacial layer that can bind to bindable agent 44. The surrounding interfacial layer typically consists of ions, inorganic molecules, and organic molecules, which can be functionalized with a surface coating to have one or more binding sites for attachment to biological molecules like the bindable agent 44. The bindable agent 44 can attach to these binding sights on one or more of the magnetic nanoparticles 42 to form a functionalized nanoparticle-bindable agent complex 46. The functionalized nanoparticle-bindable agent complex 46 can be formed before administering to the test sample or after administering to the test sample (when a concentration of the magnetic nanoparticles 42 and a concentration of bindable agent 44 are administered to the test sample to form the complex 46 in the test sample). In other words, the bindable agent 44 can be configured to bind to any instances of the disease component in the test sample to tag the disease component with the magnetic nanoparticle.

The permanent magnets 32, 34 can be movable from a position that does not affect the sample (FIG. 2) to a position that does affect the sample (FIG. 3). For example, the permanent magnets 32, 34 can be manually moved from the position that does not affect the sample to the position that does affect the sample. In another example, the permanent magnets 32, 34 can be moved in an automated fashion between the position that does not affect the sample to the position that does affect the test sample (controlled by the computer 4, a controller, one or more actuators, or the like). When in the position that affects the test sample (FIG. 3), the permanent magnets 32, 34 can create a magnetic field gradient 38 (dotted line) through the test sample. As illustrated, the magnetic field vector is perpendicular to the light beam. Please note that the permanent magnets 32, 34 need not be in the positions illustrated and, instead, can be positioned in an position that affects the test sample (magnetic field gradient "on") and any position that does not affect the test sample (magnetic field gradient "off") and the magnetic field need not be perpendicular to the light beam. Instead, the magnetic field gradient must only be established across the sample.

As show in in FIG. 3, the light source 22 can transmit a light beam 36 (dashed line) through the sample holder 24 to a light detector of the measurement device 26. The light source 22 can include a laser light source. The light from the laser light source can be polarized by a polarizer (e.g., a linear polarizer, a circular polarizer, or the like). A beam splitter can also be part of the light source 22. The beam splitter can aid in power control and/or data collection. For example, the beam splitter can provide a first portion of the light beam through the sample holder 24 and send a second portion to another detector (not shown). The detected second portion can be used to normalize the intensity of the light beam detected by the measurement device 26 after traveling through the sample in the sample holder 24.

The light detector of the measurement device 26 can detect the light beam that has travelled through the sample in the sample holder 24. The light detector can detect the light when the permanent magnets 32, 34 are in a first magnetic state position (not affecting the test sample, shown in FIG. 2) and/or when the permanent magnets are in a second magnetic state position (affecting the test sample, shown in FIG. 3). The light detector can take samples of the light signal with the permanent magnets 32, 34 in either position and/or both positions.

Figure 8:
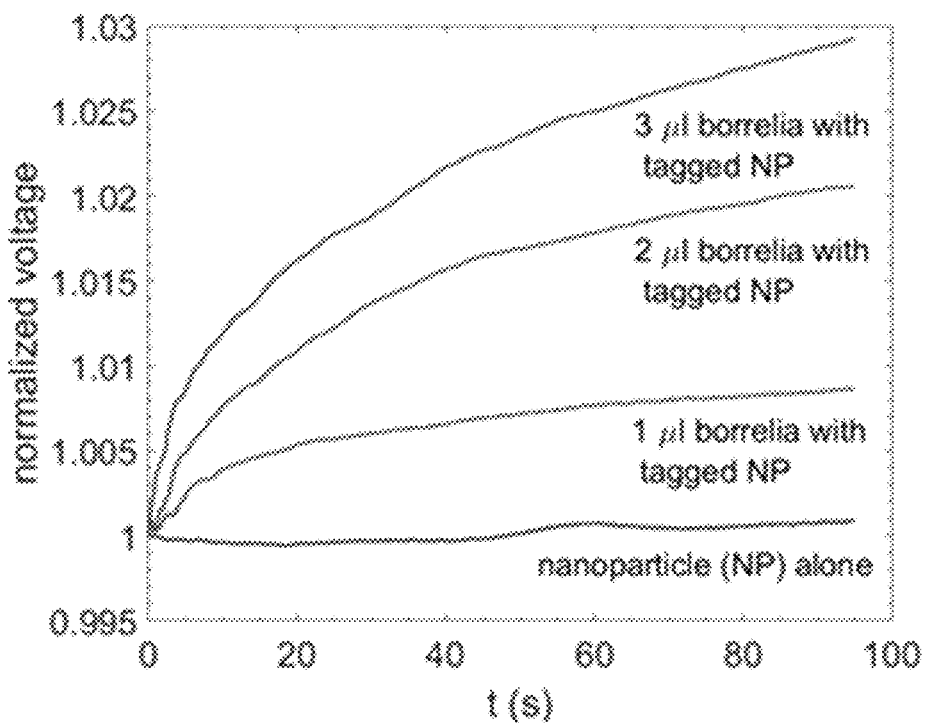
FIG. 8 shows a plot of light intensity as a function of time for three different concentrations of *Borrelia burgdorferi* bacteria tagged with nanoparticles and a control with just the nanoparticles.
Figure 9:
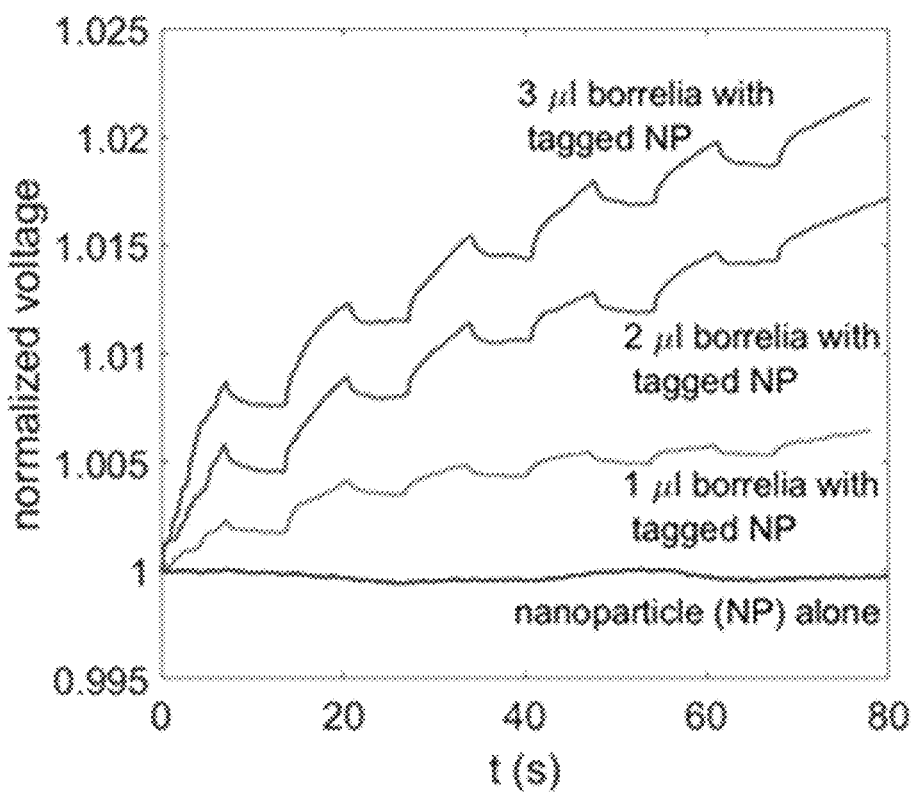
FIG. 9 shows a plot of the light intensity as a function of time for three different concentrations of *Borrelia burgdorferi* bacteria tagged with nanoparticles and a control with just the nanoparticles when the magnetic field is turned on and off cyclically.
Figure 10:
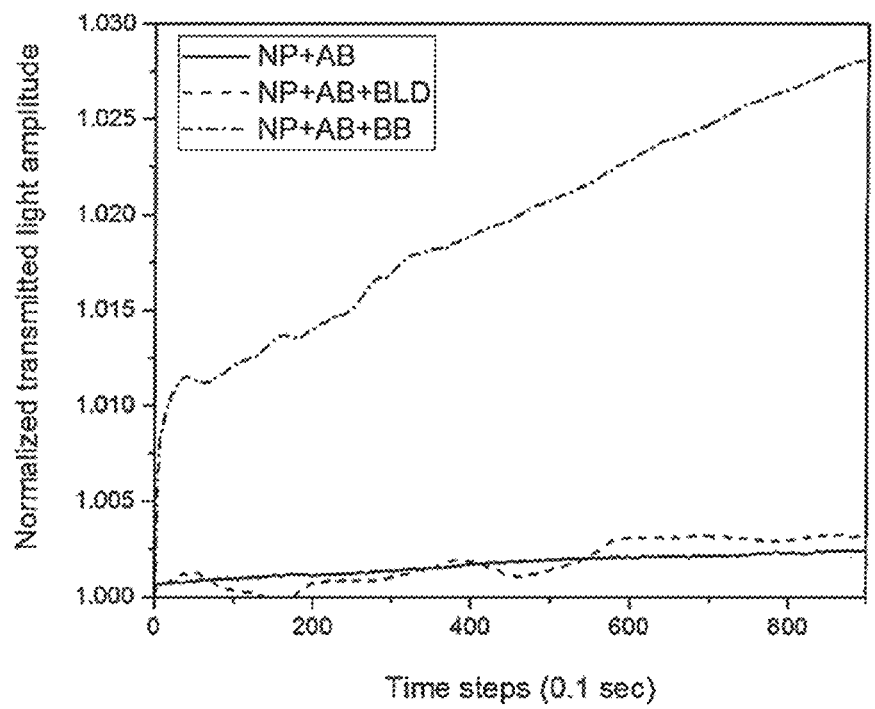
FIG. 10 shows a plot of a light response (the normalized transmission signal intensity) of different samples (*Borrelia burgdorferi* bacteria tagged with the nanoparticles and antibodies (NP+AB+BB) were compared to the nanoparticles functionalized with the antibody (NP+AB) and the NP+AB in a healthy blood sample (NPP+AB+BLD)) with a magnetic field being suddenly applied at t=0.

As an example, the light detector of the measurement device 26 can include one or more photodetectors. The measurement device 26 can also include a sampling device, which can control data acquisition by sampling the light detector over a time period according to a sampling frequency. The sampling frequency can differ based on the application. As an example, the sampling frequency can be sufficient to sample the light detector to determine transmission intensities of the light beam 36. The transmission intensities can reveal if the disease component exists in the test sample. It the transmission intensities experience a variable intensity change pattern during a time period when under the magnetic field gradient, the disease component can be determined to exist. An example of the variable intensity change pattern is shown in FIGS. 8-10. However, if the transmission intensities remain approximately constant, or steady state, the disease component can be determined not to exist in the test sample.

Lyme disease is notoriously hard to diagnose. When diagnosed early, Lyme disease can be treated with antibiotics. However, when left undiagnosed, Lyme disease can cause long term physical and mental tolls and be difficult to eliminate. As an example, a patient may have a tick bite, live in an area known for Lyme disease, or have recently traveled to an area where Lyme disease occurs. Additionally or alternatively, the patient may present with one or more symptoms of Lyme disease, including fever, chills, headache, fatigue, muscle and joint aches, swollen lymph nodes, erythema migrans (EM) rash, neck stiffness, arthritis with severe joint pain, facial palsy, shooting pains, numbness, tingling in the hands of feet, inflammation of the brain or spinal cord, episodes of dizziness or shortness of breath, heart palpitations, and/or any other symptoms that may have an association with Lyme disease. A biofluid sample can be taken from the patient. The biofluid can be blood, urine, synovial fluid, cerebrospinal fluid, or the like. The blood sample may include *Borrelia burgdorferi* bacteria, a bacterium of the spirochete class that is the most prevalent Lyme disease bacteria in North America.

At least a portion of the biofluid sample can be processed through chemical methods and then diluted with phosphate buffered saline (PBS) solution and placed in a sample holder. Magnetic nanoparticles 42 can be administered to the test sample with an anti-*Borrelia burgdorferi* antibody (a type of bindable agent 44 that specifically binds with the bacteria). The nanoparticles can be functionalized by the antibody to create a nanoparticle-antibody complex 46.

The sample with the functionalized nanoparticles is placed in the path of a light beam 36. A magnetic field is then turned on (e.g., by moving one or more permanent magnets 32, 34 into proximity of the test sample in the sample holder 24) creating a magnetic field gradient. The light detector of the measurement device 26 can record an intensity of the light beam 36 under the magnetic field gradient. Without the *Borrelia burgdorferi* bacteria, the light detector of the measurement device 26 can record a steady state or relatively steady state intensity of the light signal. However, with the *Borrelia burgdorferi* bacteria, the light detector of the measurement device 26 can record a change in the intensity of the light signal that exhibits a variable intensity change pattern. For example, the light detector 26 can record an increase in intensity for a time until a steady state is reached when the *Borrelia burgdorferi* bacteria is included in the sample.

Figure 6:
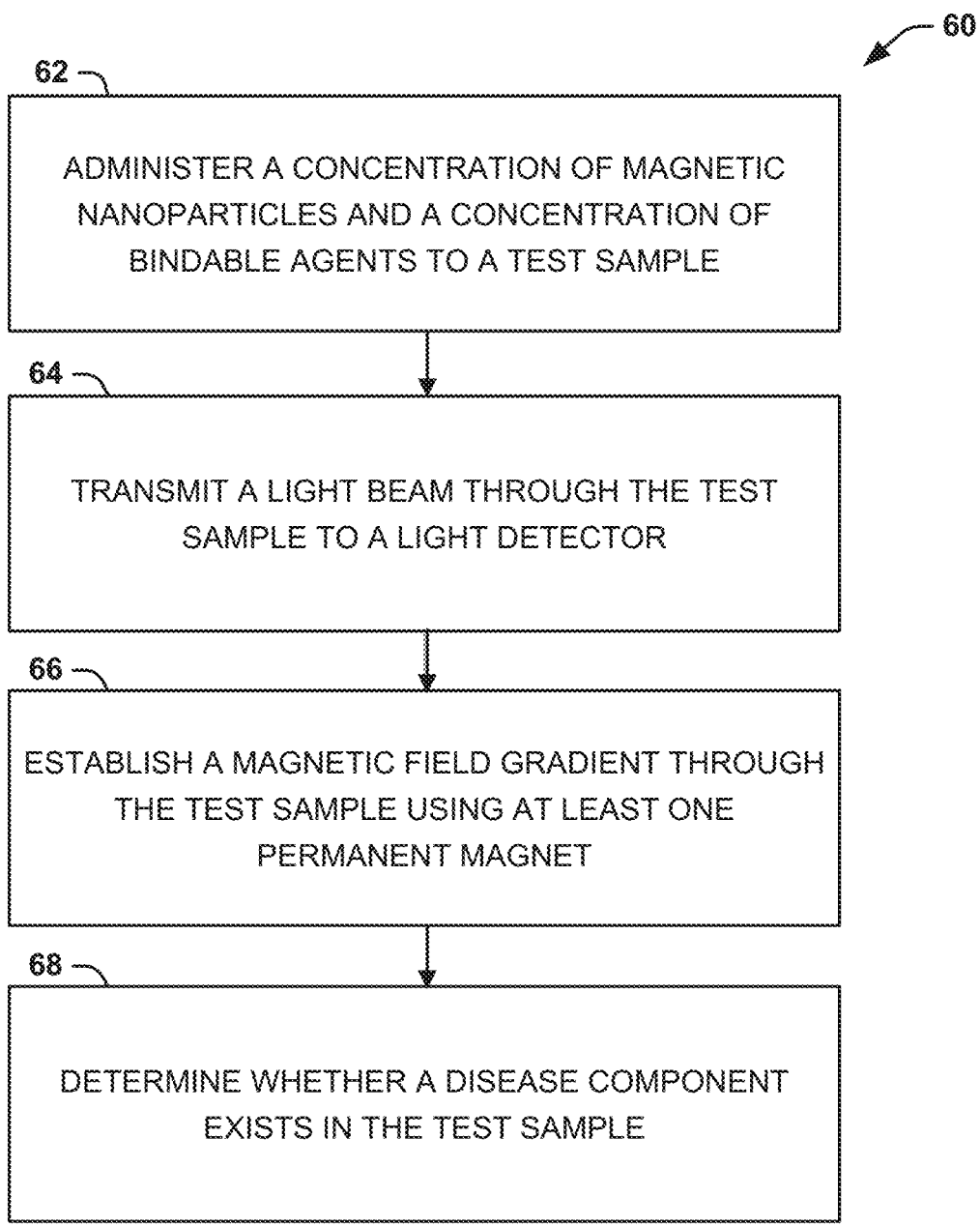
FIG. 6 is a process flow diagram of an example method for detecting a disease component using magnetic nanoparticles.

In view of the foregoing structural and functional features described above, example methods will be better appreciated with reference to FIG. 6. While, for purposes of simplicity of explanation, the method of FIG. 6 is shown and described as executing serially, it is to be understood and appreciated that the present invention is not limited by the illustrated order, as some actions could, in other examples, occur in different orders from that shown and described herein or could occur concurrently. It will be appreciated that some or all acts of this method 60 can be implemented as machine-readable instructions on a non-transitory computer readable medium.

FIG. 6 illustrates an example of a method 60 for detecting a disease component using magnetic nanoparticles. For example, the disease component can be a pathogenic bacteria, virus, fungus, cancer cell, or the like. One or more magnetic nanoparticles can attach to a bindable agent specific to the disease component. The bindable agent can be, for example, an antibody specific for a particular disease component, a ligand specific for a particular disease component, or an aptamer specific for a particular disease component.

At element 62, a concentration of magnetic nanoparticles (e.g., including magnetic nanoparticle 42) and a concentration of bindable agents (e.g., including bindable agent 44) can be administered to a test sample (e.g., test sample, examples shown in 52 and 54 of FIG. 5). Either before administration or after administration, at least a portion of the magnetic nanoparticles can attach to the bindable agents (e.g., to form NP-BA complex 46). The bindable agents can be configured to attach to a specific disease component under investigation in the test sample (e.g., shown in 54 of FIG. 5). The magnetic nanoparticles attached to the bindable agents can functionalize any of the specific disease component under investigation existing in the test sample.

The test sample can be placed in a magneto-optical detection system (e.g., magneto-optical detection system 2). At element 64, a light beam (e.g., light beam 36) can be transmitted through the test sample to a light detector (e.g., light detector of the measurement device 26). At element 66, a magnetic field gradient (e.g., magnetic field gradient 38) can be established through the test sample using at least one permanent magnet (e.g., permanent magnet 32 and/or 34). As an example, when two permanent magnets are used to establish the magnetic field gradient, the resultant magnetic field lines can be perpendicular to the light beam. However, the magnetic field lines can be established in different orientations depending on the disease component under investigation.

At element 68, a determination can be made of whether a disease component exists in the test sample (the determination can be made by the computing device 4 based on information received by the light detector of the measurement device 26). The determination can be made based on the intensity of the transmitted light beam at the detector over time. As an example, the disease component can exist if a change in intensity of the transmitted light beam under the magnetic field gradient is seen over time (this intensity change is shown in FIGS. 8-10, for example). The radius of the disease component can be»than a radius of one of the magnetic nanoparticles attached to the bindable agent. A drift speed of the disease component whose surface is covered with bindable agents each attached to one of the magnetic nanoparticles is»a drift speed of the bindable agent attached to one of the magnetic nanoparticles in the presence of the magnetic field gradient.

In other words, when the disease component is present, the transmitted light can exhibit a variable intensity change during a time period (e.g., an increase in intensity to a constant steady state), the disease component can be determined to exist. If this variable intensity change is not seen during the time period (e.g., remaining at or near steady state without the increase), the disease component can be determined not to exist. The time can be a period beginning at the time the magnetic field gradient is introduced until the end of the period (e.g., at least 60 seconds, at least 80 seconds, at least 100 seconds, at least 5 minutes, etc.). As an example, the change in intensity can be matched to a pattern predetermined to be characteristic of the specific disease component to diagnose the disease component.

In cases where the specific disease component is determined to be present in the test sample, a disease or condition in the patient can be diagnosed. The diagnosing can include performing a differential analysis on the test sample to determine the function of the disease component on the patient. For example, a treatment can be chosen based on the differential analysis.

Example

The following example is for the purpose of illustration only and is not intended to limit the scope of the appended claims. This example shows the feasibility of using magneto-optical detection of a disease component in biofluid using magnetic nanoparticles.

Model Solution Including Spherical Bacteria

A phosphate buffered saline (PBS) solution was used to model biofluid. A concentration of a spherical bacteria with a radius R was included in the PBS solution.

Magnetic Nanoparticles

A number of magnetic nanoparticles, each of radius r«R, were added to the PBS solution. The surface of the spherical bacteria became covered with the nanoparticles. Remaining nanoparticles that did not cover the surface of the spherical bacteria floated free in the PBS solution.

Application of Magnetic Field Gradient

The PBS solution included a suspension of (1) bacteria covered with nanoparticles and (2) unbound nanoparticles. A magnetic field gradient was applied to the suspension so that the bacteria were drawn toward regions of larger magnetic field strength. Because r«R, the bacteria (coated with nanoparticles) were drawn with much larger speeds than the drift speeds of the unbound nanoparticles.

The ratio of the bacteria drift speed to the unbound nanoparticle drift speed is given by $U_{cell}/U_{NP}=4R/r$. For example, if the bacteria cells are 10 microns in diameter (R=5 microns) and the nanoparticles are 10 nm in diameter (r=5 nm), the cells will move with a speed that is 4000 times that of the nanoparticles. The ratio is derived as follows.

The drag force on a single nanoparticle moving through a fluid is given by Stokes law $$F_{d,NP}=6\pi\eta r U_{NP} \quad (1)$$

where $\eta$ is the dynamic viscosity of the fluid, r is the radius of the nanoparticle, and $U_{NP}$ is the speed of the nanoparticle. The magnetic force on the nanoparticle is given by:

$$F_{m,NP} = \frac{\chi_V N_{NP}}{\mu_0} B|\nabla B| \quad (2)$$

where $\chi_V$ is the volume magnetic susceptibility of the nanoparticle, $V_{NP}$ is the volume of the nanoparticle, $\mu_0$ is the vacuum permeability, B is the magnetic field strength, and $|\nabla B|$ is the magnitude of the magnetic field gradient. Equating the magnetic force to the drag force and solving for $U_{NP}$ gives $$U_{NP} = \frac{\chi_V N_{NP}}{6\pi\mu_0 \eta r} B|\nabla B| \quad (3)$$

Assuming that the radius of a nanoparticle is much less than the radius of the cell, the drag force on the cell covered with nanoparticles is given by:

$$F_{d,cell}=6\pi\eta R U_{cell} \quad (4)$$

where $U_{cell}$ is the speed of the cell. Now the magnetic force on a cell covered with nanoparticles is simply equal to the magnetic force on a single nanoparticle multiplied by the number of nanoparticles $N_{NP}$. So the magnetic force on the cell is $$F_{m,cell} = \frac{N_{NP}\chi_V V_{NP}}{\mu_0} B|\nabla B| \quad (5)$$

Equating Eq. (4) to Eq. (5) gives for the drift speed of a cell $$U_{cell} = \frac{N_{NP}\chi_V V_{NP}}{6\pi\mu_0 \eta R} B|\nabla B| \quad (6)$$

To find the number of nanoparticles covering the cell, assume that the radius of a nanoparticle is much less than the radius of the spherical cell. Then the number of nanoparticles is given by the surface area of the cell divided by the cross-sectional area of a nanoparticle $$N_{NP} = \frac{4\pi R^2}{\pi r^2} \quad (7)$$

Inserting this into Eq. (6) gives:

$$U_{cell} = \frac{R\chi_V V_{NP}}{6\pi\mu_0 \eta r^2} B|\nabla B| \quad (8)$$

Dividing Eq. (8) by Eq. (3) gives for the ratio of the drift speed of the cell to that of a single nanoparticle $$\frac{U_{cell}}{U_{NP}} = \frac{4R}{r} \quad (9)$$

Since the radius of the cell is much larger than the radius of a nanoparticle, the drift speed of the cell is much larger than that of an individual nanoparticle. Equation 9 assumes that the entire surface of the bacteria is covered with nanoparticles. If, for example, only a quarter of the surface were covered with nanoparticles, the ratio of the drift speeds would be one quarter as much.

Application of Magnetic Field Gradient and Light

When a light beam is directed through the sample, the magnetic field gradient draws the bacteria away from the region containing the light beam. The intensity of the light detected following the sample will increase with time. Because the drift speed of the bacteria is so much greater than that of the nanoparticles, the rate of increase of the light intensity will be proportional to the concentration of bacteria, even though the overall concentration of the nanoparticles (both bound and unbound) may be constant.

Although in this example the bacteria are drawn away from the light beam, it is also possible to draw the bacteria into the light beam, which will decrease the intensity of the signal as more bacteria block the light. This will have the effect of concentrating the bacteria into the light beam path, thus increasing the sensitivity of the device.

Bacteria of Other Shapes

Figure 7:
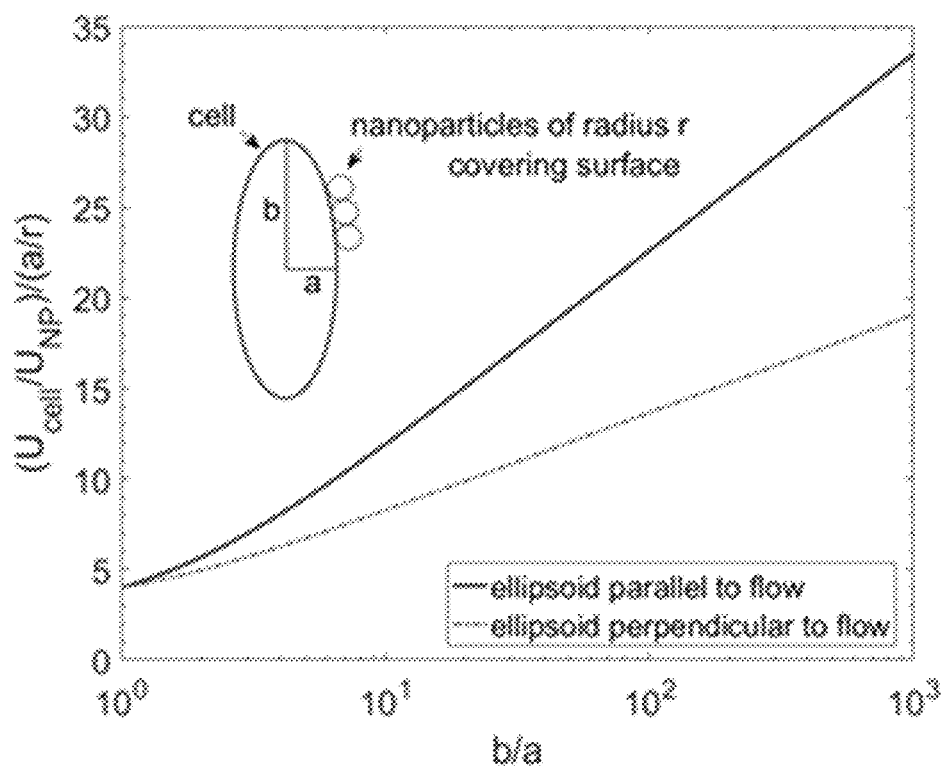
FIG. 7 shows a plot of the drift speed ratio, normalized by a/r, for various ratios of the semi-major to semi-minor axes, b/a, for an ellipsoidal-shaped cell.

To see that other bacterial shapes have similar drift speed properties, FIG. 7 shows a plot of the drift speed ratio for an ellipsoid, normalized by a/r, for various ratios of the semi-major to semi-minor axes, b/a, for an ellipsoidal shaped cell. For example, if a=50 nm, b=5 microns, and r=5 nm, the cell will move with a speed that is about 100 to 200 times that of the unbound nanoparticles. Also it may be noted that since the cells tend to align themselves along the direction of the magnetic field gradient, the cells would drift with an orientation along the flow direction and thus drift at the larger of the two speeds, i.e. parallel to flow.

Borrelia burgdorferi Bacteria

Borrelia burgdorferi is a bacterium of the spirochete class that is about 0.3 μm wide and 5 to 20 μm long that causes Lyme Disease—the most prevalent Lyme Disease bacteria in North America. The Borrelia burgdorferi was obtained as a frozen live sample from BEI Resources (Manassas, VA). Samples containing Borrelia burgdorferi at different concentrations were prepared from the frozen source by diluting into a Phosphate buffered saline (PBS) solution. 10 nanometer nanoparticles were functionalized with anti-Borrelia burgdorferi antibody and introduced into the PBS diluted Borrelia burgdorferi samples.

FIG. 8 shows a plot of the light intensity as a function of time for three different concentrations of Borrelia burgdorferi, which reveals the dependence of the change in light passing through the sample on the concentration of bacteria within the sample. A magnetic field was applied to each of the samples at t=0. For all four curves, the concentration of nanoparticles was 0.2 μg/ml. As seen from this plot, the light intensity increases more rapidly for larger Borrelia burgdorferi concentrations. It should be noted that a portion of the initial increase in intensity is related to the initial rotation of the bacteria with the application of the magnetic field.

To see that the magnetic field also causes rotation of the bacteria, FIG. 9 shows what happens if the magnetic field is turned on and off cyclically. As seen from this figure, there is an oscillation in the signal, as well as the steady increase. This may be explained by rotation of the bacteria. With no field, the bacteria are randomly oriented. When the field is initially applied at t=0, the bacteria become aligned with the field gradient, causing the signal to increase. When the field is again removed, the bacteria again become randomly oriented, as a result of Brownian motion of the molecules in the fluid, and the signal decreases. Since the bacteria are also drawn toward regions of higher magnetic field strength, there is also the steady increase in signal superimposed on this oscillation.

Although both the steady increase and the oscillation are noticeable in the signal for the Borrelia burgdorferi, only one feature may dominate for other pathogens, depending on the size and shape of the pathogen. For example, if the pathogen is near spherical, there will be little oscillation and the steady increase will dominate. If instead the pathogen deviates significantly from being spherical, then if a pathogen is very large, the rotation rate may be so slow that the steady increase in signal will dominate. If the pathogen is very small, the rate at which it is drawn toward regions of higher magnetic field strength will be very slow, and the rotational effects may dominate.

The light response of Borrelia burgdorferi bacteria with the nanoparticles and antibodies (NP+AB+BB) were compared to the nanoparticles functionalized with the antibody (NP+AB) and the NP+AB in a healthy blood sample (NPP+AB+BLD). FIG. 10 shows a plot of the transmitted light intensity for sample NP+AB, sample NP+AB+BLD, and a sample of NP+AB+BB. The sample containing the BB shows an initial rapid increase in transmitted light intensity then a gradual increase. Both the NP+AB and the NP+AB+

BLD samples exhibit transmitted light intensities that remain approximately constant.

The aspects of this disclosure have been described illustratively. Accordingly, the terminology employed throughout the disclosure should be read in an exemplary rather than a limiting manner. Although minor modifications of the invention will occur to those well versed in the art, it shall be understood that what is intended to be circumscribed within the scope of the patent warranted hereon are all such embodiments that reasonably fall within the scope of the advancement to the art hereby contributed, and that that scope shall not be restricted.

References to "one embodiment", "an embodiment", "some embodiments", "one example", "an example", "some examples" and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

Where the disclosure or claims recite "a," "an," "a first," or "another" element, or the equivalent thereof, it should be interpreted to include one or more than one such element, neither requiring nor excluding two or more such elements. Furthermore, what have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims.

What is claimed is:

1. An in-vitro method for detecting a disease component in a test sample taken from a patient, the method comprising:
   administering a concentration of magnetic nanoparticles and a concentration of bindable agents to the test sample in a sample holder, wherein the test sample comprises a biofluid taken from a patient to be tested for a disease component and each of the bindable agents are configured to attach to a plurality of the magnetic nanoparticles and the disease component;
   transmitting a light beam through the test sample in the sample holder to a light detector;
   establishing a magnetic field gradient through the test sample while the light beam is transmitted;
   determining whether a disease component exists in the test sample when a change in intensity of the transmitted light beam under the magnetic field gradient exhibits a variable intensity change pattern during a time period,
   wherein the determining comprises matching the change in intensity to a predetermined pattern; and
   diagnosing a disease or condition in a patient based on the disease component existing in the test sample.

2. The method of claim 1, wherein the predetermined pattern is established based on the disease.

3. The method of claim 1, wherein the bindable agents are configured to attach to the disease component in the test sample to tag the disease component in the sample with the magnetic nanoparticles.

4. The method of claim 3, wherein a radius of the disease component is greater than a radius of one of the magnetic nanoparticles attached to the bindable agent.

5. The method of claim 1, wherein the disease component is a bacteria, a virus, a fungus, or a cancer cell.

6. The method of claim 1, wherein the bindable agent is an antibody specific for the disease component, a ligand specific for the disease component, or an aptimer specific to the disease component.

7. The method of claim 1, wherein the diagnosing further comprises performing a differential analysis on the test sample when the disease component exists in the test sample to diagnose the disease or condition.

8. The method of claim 1, wherein the magnetic field is established between two magnets so that the resultant magnetic field lines are perpendicular to the light beam.

9. The method of claim 1, wherein the variable intensity change pattern is based on a drift speed of the disease component tagged by the plurality of magnetic nanoparticles.

10. An in-vitro method for detecting a disease component in a test sample taken from a patient, the method comprising:
    administering a concentration of magnetic nanoparticles and a concentration of bindable agents to the test sample in a sample holder,
    wherein the test sample comprises a biofluid taken from the patient,
    wherein each the bindable agents are configured to attach to a plurality of the magnetic nanoparticles and the disease component in the test sample to tag the disease component in the sample with the magnetic nanoparticles, and
    wherein a radius of the disease component is greater than a radius of one of the magnetic nanoparticles attached to the bindable agent;
    transmitting a light beam through the test sample in the sample holder to a light detector;
    establishing a magnetic field gradient through the test sample while the light beam is transmitted; and
    determining whether a disease component exists in the test sample when a change in intensity of the transmitted light beam under the magnetic field gradient exhibits a variable intensity change pattern during a time period,
    wherein the determining comprises matching the change in intensity to a predetermined pattern.

11. An in-vitro method for detecting a disease component in a test sample taken from a patient, the method comprising:
    administering a concentration of magnetic nanoparticles and a concentration of bindable agents to the test sample in a sample holder, wherein the test sample comprises a biofluid taken from a patient to be tested for a disease component and each of the bindable agents are configured to attach to a plurality of the magnetic nanoparticles and the disease component;
    transmitting a light beam through the test sample in the sample holder to a light detector;
    establishing a magnetic field gradient through the test sample while the light beam is transmitted; and
    determining whether a disease component exists in the test sample when a change in intensity of the transmitted light beam under the magnetic field gradient exhibits a variable intensity change pattern during a time period,
    wherein the determining comprises matching the change in intensity to a predetermined pattern, and
    wherein the variable intensity change pattern is based on a drift speed of the disease component tagged by the plurality of magnetic nanoparticles.

* * * * *